(12) United States Patent
Tang

(10) Patent No.: US 12,172,324 B2
(45) Date of Patent: Dec. 24, 2024

(54) METHOD FOR DETERMINING SAFETY-LIMIT ZONE, AND DEVICE, RESET METHOD AND MEDICAL ROBOT USING THE SAME

(71) Applicant: BOE TECHNOLOGY GROUP CO., LTD., Beijing (CN)

(72) Inventor: Jinmiao Tang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 17/767,976

(22) PCT Filed: May 24, 2021

(86) PCT No.: PCT/CN2021/095555
§ 371 (c)(1),
(2) Date: Apr. 11, 2022

(87) PCT Pub. No.: WO2021/238876
PCT Pub. Date: Dec. 2, 2021

(65) Prior Publication Data
US 2024/0100701 A1 Mar. 28, 2024

(30) Foreign Application Priority Data
May 27, 2020 (CN) .......................... 202010462412.2

(51) Int. Cl.
*B25J 9/16* (2006.01)
*A61B 34/20* (2016.01)
*A61B 34/30* (2016.01)

(52) U.S. Cl.
CPC .............. *B25J 9/1674* (2013.01); *A61B 34/20* (2016.02); *A61B 34/30* (2016.02); *B25J 9/1697* (2013.01); *A61B 2034/2065* (2016.02)

(58) Field of Classification Search
CPC .......... B25J 9/1674; B25J 9/1697; B25J 9/16; A61B 34/20; A61B 34/30;
(Continued)

(56) References Cited

U.S. PATENT DOCUMENTS 4,636,699 A * 1/1987 Kato ....................... B25J 9/1692
318/563
10,015,470 B2 7/2018 Park
(Continued)

FOREIGN PATENT DOCUMENTS

CN 103750888 A 4/2014
CN 107016666 A 8/2017
(Continued)

OTHER PUBLICATIONS

Written Opinion from PCT/CN2021/095555 dated Aug. 20, 2021.
(Continued)

*Primary Examiner* — Abby Y Lin
*Assistant Examiner* — Karston G. Evans
(74) *Attorney, Agent, or Firm* — Calfee, Halter & Griswold LLP

(57) ABSTRACT

A method for determining a safety-limit zone, including: obtaining a first image from a limb taken from a first direction, wherein the first image includes a first effective area and a second effective area, and the first effective area is capable of matching with the second effective area; obtaining a second image from the limb taken from a second direction, wherein the second image includes a third effective area corresponding to the first effective area, and a fourth effective area corresponding to the second effective area, the third effective area is capable of matching with the fourth effective area, and the second direction and the first direction are perpendicular to each other; and obtaining a safety-limit zone and safety-rotation angles according to the
(Continued)

first effective area, the second effective area, the third effective area and the fourth effective area.

9 Claims, 11 Drawing Sheets

(58) Field of Classification Search
CPC ... A61B 2034/2065; A61B 6/00; A61B 6/032; A61B 6/505
See application file for complete search history.

(56) References Cited

U.S. PATENT DOCUMENTS

| | | | |
|---|---|---|---|
| 2015/0341615 | A1 | 11/2015 | Park |
| 2017/0360513 | A1* | 12/2017 | Amiot ............... A61B 34/20 |
| 2021/0192759 | A1* | 6/2021 | Lang ............... A61B 34/20 |
| 2022/0234209 | A1* | 7/2022 | Kriveshko ............ B25J 9/1697 |

FOREIGN PATENT DOCUMENTS

| | | | | | |
|---|---|---|---|---|---|
| CN | 107016666 | A1 | 8/2017 | | |
| CN | 107550567 | A | 1/2018 | | |
| CN | 107550567 | A1 | 1/2018 | | |
| CN | 107811698 | A | 3/2018 | | |
| CN | 107967932 | A | 4/2018 | | |
| CN | 108392271 | A | 8/2018 | | |
| CN | 109545020 | A | 3/2019 | | |
| CN | 109688963 | A | * 4/2019 | ............ A61B 17/15 |
| CN | 109820590 | A | 5/2019 | | |
| CN | 106102633 | B | 6/2019 | | |
| CN | 109998687 | A | 7/2019 | | |
| CN | 209343565 | U | 9/2019 | | |
| CN | 107811698 | B | 4/2020 | | |
| CN | 111134842 | A | 5/2020 | | |
| CN | 210727852 | U | 6/2020 | | |
| CN | 111590584 | A | 8/2020 | | |
| WO | 2014077613 | A1 | 5/2014 | | |
| WO | 2015103712 | A1 | 7/2015 | | |
| WO | 2020088430 | A1 | 5/2020 | | |
| WO | 2020164548 | A1 | 8/2020 | | |

OTHER PUBLICATIONS

International Search Report from PCT/CN2021/095555 dated Aug. 20, 2021.
Office action from Chinese Application No. 202010462412.2 dated Mar. 23, 2021.
Written Opinion from PCT/CN2021/095555 dated Aug. 19, 2021.
International Search Report from PCT/CN2021/095555 dated Aug. 19, 2021.

* cited by examiner

| Obtaining a first image from a limb taken from a first direction, wherein the first image comprises a first effective area and a second effective area, and the first effective area is capable of matching with the second effective area | — S10 |

| Obtaining a second image from the limb taken from a second direction, wherein the second image comprises a third effective area corresponding to the first effective area, and a fourth effective area corresponding to the second effective area, the third effective area is capable of matching with the fourth effective area, and the second direction and the first direction are perpendicular to each other | — S20 |

| Obtaining a safety-limit zone and safety-rotation angles according to the first effective area, the second effective area, the third effective area and the fourth effective area | — S30 |

FIG. 1

METHOD FOR DETERMINING SAFETY-LIMIT ZONE, AND DEVICE, RESET METHOD AND MEDICAL ROBOT USING THE SAME

CROSS REFERENCE TO RELATED APPLICATION

This application claims priority to International Application No. PCT/CN2021/095555, filed on May 24, 2021 which claims the priority of a Chinese patent application filed on May 27, 2020 with application number 202010462412.2 entitled "SAFETY LIMIT REGION DETERMINATION METHOD AND DEVICE, RESETTING METHOD, AND MEDICAL ROBOT", the entire contents of which Incorporated herein by reference in its entirety.

TECHNICAL FIELD

The present disclosure relates to the technical field of medical devices, and in particular, to a method for determining a safety-limit zone, a device for determining a safety-limit zone, a reset method, and a medical robot including the device for determining the safety-limit zone.

BACKGROUND

At present, limit of robot is mainly by adding limit modules at joints. When the robot reaches the limit, the robot is stopped through collision. What the limit protects is internal cables of the robot, to make them not be twisted and damaged due to excessive rotation of the joints. Some kinds of limit are to pre-store a plurality of safety threshold limits for surgical procedures, and boundary data of the safety threshold limits should be approximate values set by doctors based on specific experience.

However, for a fractured patient, fractures may occur in any part of human body, so the specific boundary data can only be set according to an actual fracture condition of the patient, and which has no possibility to be set and stored in advance.

Therefore, it is necessary to study a method for determining a safety-limit zone, a device for determining a safety-limit zone, a reset method, and a medical robot including the device for determining the safety-limit zone.

It should be noted that the information disclosed in the above background section is only for enhancing understanding of the background of the present disclosure, and therefore may include information that does not form the prior art known to a person of ordinary skill in the art.

SUMMARY

The purpose of the present disclosure is to overcome the above-mentioned deficiencies of the prior art, and to provide a method for determining a safety-limit zone, a device for determining a safety-limit zone, a reset method, and a medical robot including the device for determining a safety-limit zone.

According to an aspect of the present disclosure, a method for determining a safety-limit zone is provided, including:
  obtaining a first image from a limb taken from a first direction, wherein the first image includes a first effective area and a second effective area, and the first effective area is capable of matching with the second effective area;
  obtaining a second image from the limb taken from a second direction, wherein the second image includes a third effective area corresponding to the first effective area, and a fourth effective area corresponding to the second effective area, the third effective area is capable of matching with the fourth effective area, and the second direction and the first direction are perpendicular to each other; and
  obtaining a safety-limit zone and safety-rotation angles according to the first effective area, the second effective area, the third effective area and the fourth effective area.

In an exemplary embodiment of the present disclosure, obtaining a safety-limit zone and safety-rotation angles according to the first effective area, the second effective area, the third effective area and the fourth effective area, includes:
  establishing a three-dimensional-rectangular-coordinate system with a coordinate origin point that is a contact point between a manipulator and the limb;
  obtaining a first matching curve matching with the second effective area on the first effective area, and obtaining a second matching curve matching with the first effective area on the second effective area;
  obtaining a plurality of first matching points on the first matching curve, and obtaining a plurality of second matching points on the second matching curve, wherein the plurality of first matching points and the plurality of second matching points are matched to each other one-to-one;
  obtaining a third matching curve matching with the fourth effective area on the third effective area, and obtaining a fourth matching curve matching with the third effective area on the fourth effective area;
  obtaining a plurality of third matching points on the third matching curve, and obtaining a plurality of fourth matching points on the fourth matching curve, wherein the plurality of third matching points and the plurality of fourth matching points are matched to each other one-to-one; and
  obtaining the safety-limit zone according to the plurality of first matching points, the plurality of second matching points, the plurality of third matching points and the plurality of fourth matching points.

In an exemplary embodiment of the present disclosure, obtaining the safety-limit zone according to the plurality of first matching points, the plurality of second matching points, the plurality of third matching points and the plurality of fourth matching points, includes:
  calculating first straight-line distances between the respective first matching points and the corresponding respective second matching points on a first axial direction, and calculating a first average value of the first straight-line distances;
  calculating second straight-line distances between the respective first matching points and the corresponding respective second matching points on a second axial direction, and calculating a second average value of the second straight-line distances;
  calculating third straight-line distances between the respective third matching points and the corresponding respective fourth matching points on the second axial direction, and calculating a third average value of the third straight-line distances;
  calculating fourth straight-line distances between the respective third matching points and the corresponding respective fourth matching points on a third axial direction, and calculating a fourth average value of the fourth straight-line distances; and determining the safety-limit zone as a cuboid with a center point being the coordinate origin point, wherein a length side of the cuboid is parallel to the first axial direction, a length value of the cuboid is greater than or equal to the first average value, a width side of the cuboid is parallel to the second axial direction, a width value of the cuboid is greater than or equal to the second average value or the third average value, a height side of the cuboid is parallel to the third axial direction, and a height value of the cuboid is greater than or equal to the fourth average value.

In an exemplary embodiment of the present disclosure, the second average value is greater than the third average value, and the width value of the cuboid is greater than or equal to the second average value.

In an exemplary embodiment of the present disclosure, the length value of the cuboid is larger than the first average value by 2-3 mm, the width value of the cuboid is larger than the second average value by 2-3 mm, and the height value of the cuboid is greater than the fourth average value by 2-3 mm.

In an exemplary embodiment of the present disclosure, obtaining safety-rotation angles according to the first effective area, the second effective area, the third effective area and the fourth effective area, includes:

obtaining a first inclination angle of a first boundary-line segment connected with the first matching curve relative to the first axial direction on the first effective area;

obtaining a second inclination angle of a second boundary-line segment connected with the second matching curve relative to the first axial direction on the second effective area, wherein the first boundary-line segment and the second boundary-line segment are capable of being matched as one line segment;

obtaining a third inclination angle of a third boundary-line segment connected with the third matching curve relative to the third axial direction on the third effective area;

obtaining a fourth inclination angle of a fourth boundary-line segment connected with the fourth matching curve relative to the third axial direction on the fourth effective area, wherein the third boundary-line segment and the fourth boundary-line segment are capable of being matched as one line segment; and determining that an absolute value of a difference value between the first inclination angle and the second inclination angle is equal to or less than the safety-rotation angle relative to the third axial direction, and an absolute value of a difference value between the third inclination angle and the fourth inclination angle is equal to or less than the safety-rotation angle relative to the first axial direction.

In an exemplary embodiment of the present disclosure, the safety-rotation angle relative to the third axial direction is 105-110% of the absolute value of the difference value between the first inclination angle and the second inclination angle, and the safety-rotation angle relative to the first axial direction is 105-110% of the absolute value of the difference value between the third inclination angle and the fourth inclination angle.

According to one aspect of the present disclosure, there is provided a reset method, including:

obtaining a reset-starting point and a reset-ending point;
determining a reset direction and a reset distance, wherein the reset direction is a direction from the reset-starting point to the reset-ending point, and the reset distance is a straight-line distance between the reset-starting point and the reset-ending point;

obtaining an included angle between the reset direction and a first axial direction, and obtaining reset-translation amount on respective coordinate axes according to the included angle;

obtaining a reset-rotation angle, and performing reset according to the reset-translation amount and the reset-rotation angle;

obtaining real-time-displacement amount and real-time-rotation angles, determining whether the real-time-displacement amount is within the safety-limit zone determined by the above method for determining a safety-limit zone, and determining whether the real-time-rotation angles are within ranges of the safety-rotation angles determined by the above method for determining a safety-limit zone; and if the real-time-displacement amount exceeds the safety-limit zone, or the real-time-rotation angles exceed the ranges of the safety-rotation angles, stopping reset operation.

According to an aspect of the present disclosure, a device for determining a safety-limit zone is provided, including:

a first obtaining unit, configured to obtain a first image from a limb taken from a first direction, wherein the first image includes a first effective area and a second effective area, and the first effective area is capable of matching with the second effective area;

a second obtaining unit, configured to obtain a second image from the limb taken from a second direction, wherein the second image includes a third effective area corresponding to the first effective area, and the fourth effective area corresponding to the second effective area, the third effective area is capable of matching with the fourth effective area, and the second direction and the first direction are perpendicular to each other; and a determining unit, configured to obtain a safety-limit zone and safety-rotation angles according to the first effective area, the second effective area, the third effective area and the fourth effective area.

According to one aspect of the present disclosure, there is provided a medical robot, including:

a manipulator;
the device for determining a safety-limit zone according to claim 9;
a rotation sensor, configured to measure real-time-rotation angles of the manipulator; and
a controller, having an input end electrically connected to an output end of the rotation sensor, and an output end electrically connected to a control end of the manipulator, wherein the controller is configured to control start and stop of the manipulator according to measurement values of the rotation sensor, and a safety-limit zone and safety-rotation angles determined by the device for determining a safety-limit zone.

The method for determining a safety-limit zone of the present disclosure obtains a first image from a limb taken from a first direction, the first image includes a first effective area and a second effective area, and the first effective area is capable of matching with the second effective area. A second image from the limb taken from the second direction is obtained, the second image includes a third effective area corresponding to the first effective area, and a fourth effective area corresponding to the second effective area, the third effective area is capable of matching with the fourth effective area, and the second direction is perpendicular to the first direction. The safety-limit zone and the safety-rotation angles are obtained according to the first effective area, the second effective area, the third effective area and the fourth effective area. Different safety-limit zones and safety-rotation angles may be set for different fractured patients.

It shall be understood that the foregoing general description and the following detailed description are exemplary and explanatory only and are not limiting of the present disclosure.

BRIEF DESCRIPTION OF THE DRAWINGS

The accompanying drawings, which are incorporated in and constitute a part of this specification, illustrate embodiments consistent with the disclosure and together with the description serve to explain the principles of the disclosure. Apparently, the drawings in the following description are only some embodiments of the present disclosure, and for those of ordinary skill in the art, other drawings may be obtained from these drawings without creative efforts as well.

FIG. 1 is a flow chart that schematically shows an exemplary embodiment of a method for determining a safety-limit zone of the present disclosure.

Figure 2:
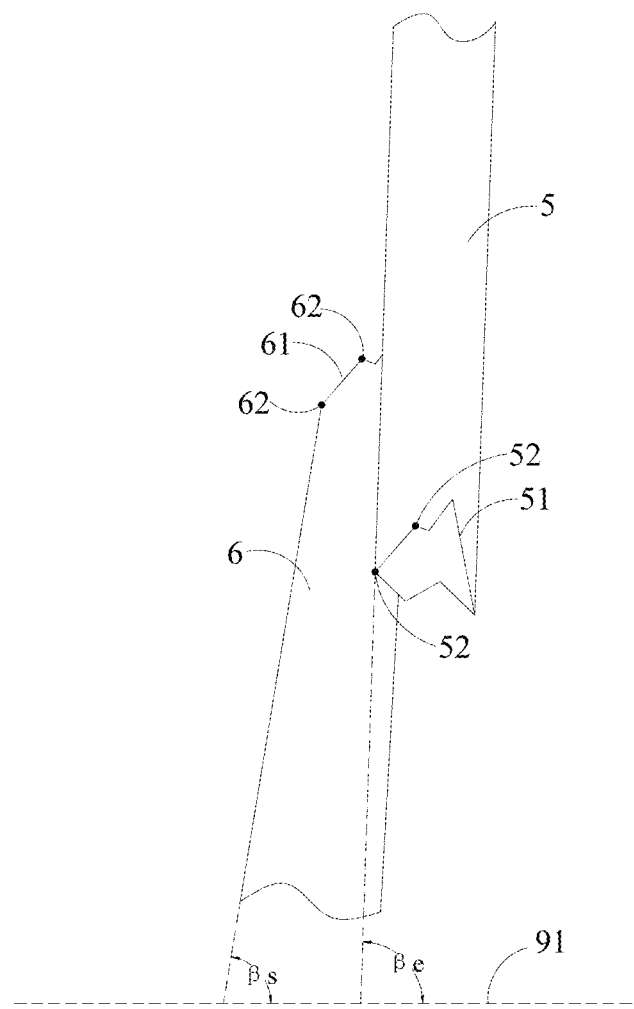
FIG. 2 is a structural diagram that schematically shows image processing on a first image.

DESCRIPTION OF REFERENCE SIGNS 10. first obtaining unit; 20. second obtaining unit; 30. determining unit;
2. rotation sensor; 3. controller; 4. manipulator;
5. first effective area; 51. first matching curve; 52. first matching point;
6. second effective area; 61. second matching curve; 62. second matching point;
7. third effective area; 71. third matching curve; 72. third matching point;
8. fourth effective area; 81. fourth matching curve; 82. fourth matching point;
91, first axial direction; 92, third axial direction; and
101. safety-limit zone; and 102. safety-rotation angle.

DETAILED DESCRIPTION

Exemplary embodiments will now be described more fully with reference to the accompanying drawings. Exemplary embodiments, however, may be embodied in various forms and should not be construed as limited to the examples set forth herein; rather, these embodiments are provided such that this disclosure will be thorough and complete, and will fully convey the concept of exemplary embodiments to those skilled in the art. The described features, structures, or characteristics may be combined in any suitable manner in one or more embodiments. In the following description, numerous specific details are provided in order to give a thorough understanding of the embodiments of the present disclosure. However, those skilled in the art will appreciate that the technical solutions of the present disclosure may be practiced without one or more of the specific details; or other methods, components, devices, steps, etc., may be employed. In other instances, well-known solutions have not been shown or described in detail to avoid obscuring aspects of the present disclosure.

Furthermore, the drawings are merely schematic illustrations of the present disclosure and are not necessarily drawn to scale. The same reference signs in the drawings denote the same or similar parts, and thus their repeated descriptions will be omitted. Some of the block diagrams shown in the figures are functional entities that do not necessarily correspond to physically or logically separate entities. These functional entities may be implemented in software, or in one or more hardware modules or integrated circuits, or in different networks and/or processor devices and/or microcontroller devices.

The exemplary embodiment first provides a method for determining a safety-limit zone. Referring to FIG. 1, the method for determining a safety-limit zone may include the following steps:

step S10, obtaining a first image from a limb taken from a first direction, wherein the first image includes a first effective area 5 and a second effective area 6, and the first effective area 5 is capable of matching with the second effective area 6;

step S20, obtaining a second image from the limb taken from a second direction, wherein the second image includes a third effective area 7 corresponding to the first effective area 5, and a fourth effective area 8 corresponding to the second effective area 6, the third effective area 7 is capable of matching with the fourth effective area 8, and the second direction and the first direction are perpendicular to each other; and step S30, obtaining a safety-limit zone and safety-rotation angles, according to the first effective area 5, the second effective area 6, the third effective area 7 and the fourth effective area 8.

According to the method for determining the safety-limit zone in the exemplary embodiment, different safety-limit zones and safety-rotation angles may be set for different fractured patients.

Next, the method for determining the safety-limit zone in the exemplary embodiment will be further described.

In step S10, the first image from the limb taken from the first direction is obtained, wherein the first image includes the first effective area 5 and the second effective area 6, and the first effective area 5 is capable of matching with the second effective area 6.

Referring to FIG. 2, in the exemplary embodiment, the first direction may be a direction from top to bottom, that is, a third axial direction 92 (z-axis). The first image may be a CT image or an X-ray image. The limb may be a fractured limb of a fractured patient. The first effective area 5 is an image of one of two bones formed from a fractured bone, and the second effective area 6 is an image of the other one of the two bones. Therefore, the first effective area 5 is capable of matching with the second effective area 6. That is, a fracture edge of the first active area 5 is capable of matching with a fracture edge of the second active area 6. That is to say, when the CT image from the fractured limb is taken from top to bottom, there are images of two bones after fracture on the CT image, the image of the first bone is the first effective area 5, the image of the second bone is the second effective area 6, and the first effective area 5 is capable of matching with the second effective area 6 after reset.

In step S20, the second image from the limb taken from the second direction is obtained, wherein the second image includes the third effective area 7 corresponding to the first effective area 5, and the fourth effective area 8 corresponding to the second effective area 6, the third effective area 7 is capable of matching with the fourth effective area 8, and the second direction and the first direction are perpendicular to each other.

Figure 3:
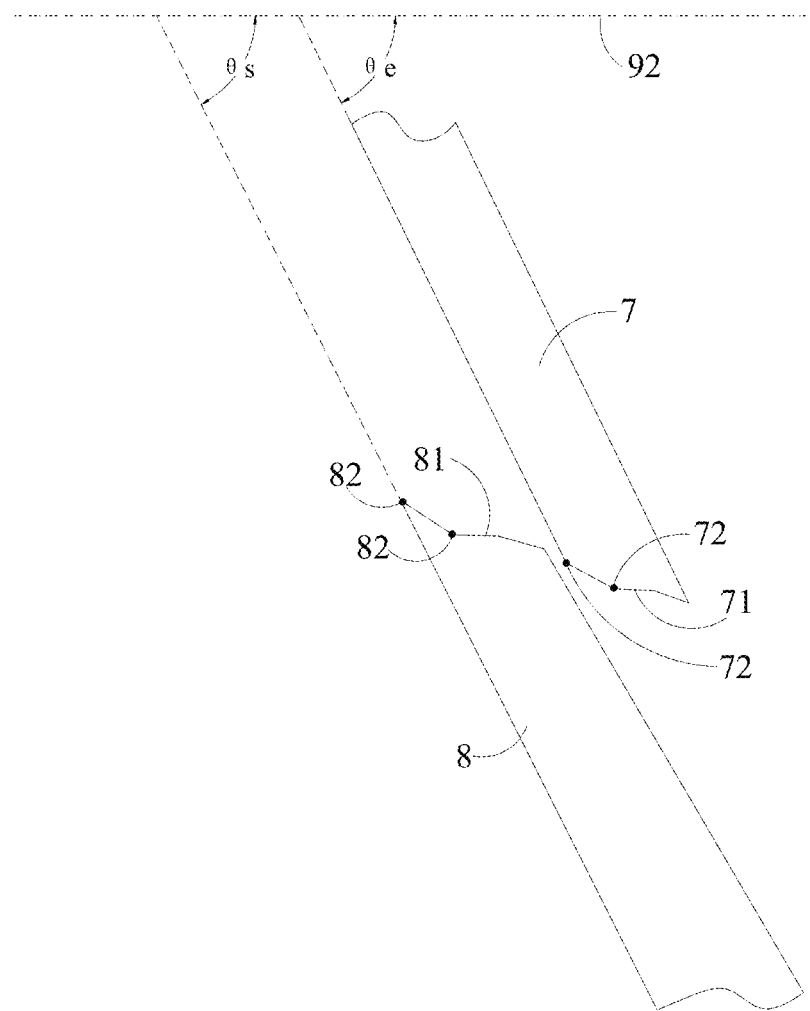
FIG. 3 is a structural diagram that schematically shows image processing on a second image.

Referring to FIG. 3, in the exemplary embodiment, the second direction may be a direction from front to back, that is, a first axial direction 91 (x-axis). The second image may be a CT image or an X-ray image. The third effective area 7 and the first effective area 5 are photographed from the same bone, but at different angles; and the fourth effective area 8 and the second effective area 6 are photographed from the same bone, but at different angles. Therefore, the third effective area 7 is capable of matching with the fourth effective area 8. That is, a fracture edge of the third effective area 7 is capable of matching with a fracture edge of the fourth effective area 8. That is to say, when the CT image from the fractured limb are taken from front to back, there are images of two bones after fracture on the CT image, the image of the first bone is the third effective area 7, the image of the second bone is the fourth effective area 8, and the third effective area 7 is capable of matching with the fourth effective area 8 after reset.

In step S30, the safety-limit zone and the safety-rotation angles are obtained according to the first effective area 5, the second effective area 6, the third effective area 7 and the fourth effective area 8.

In the exemplary embodiment, first, a three-dimensional-rectangular-coordinate system is established, with a coordinate origin point which may be any point in a contact surface between a manipulator and the limb, wherein an x-axis and a y-axis of the three-dimensional-rectangular-coordinate system may be horizontal axes, the x-axis and the y-axis are perpendicular to each other, and a z-axis is perpendicular to both the x-axis and the y-axis. The coordinate system may be set according to the work of the manipulator as well, and the coordinate system is only used as a reference, as long as it is always consistent.

Referring to FIG. 2 and FIG. 3, then, through image processing, a first matching curve 51 matching with the second effective area 6 is obtained on the first effective area 5, that is, a first fracture curve is obtained on the first effective area 5; a second matching curve 61 matching with the first effective area 5 is obtained on the second effective area 6, that is, a second fracture curve is obtained on the second effective area 6 as well; a third matching curve 71 matching with the fourth effective area 8 is obtained on the third effective area 7, that is, a third fracture curve is obtained on the third effective area 7; and a fourth matching curve 81 matching with the third effective area 7 is obtained on the fourth effective area 8, that is, a fourth fracture curve is obtained on the fourth effective area 8.

Then, through the image processing, a plurality of first matching points 52 are obtained on the first matching curve 51, and the first matching points 52 may be a starting point, a highest point, a lowest point, or a point at a position of a maximum curvature radius on the first fracture curve, etc. A plurality of second matching points 62 are obtained on the second matching curve 61, and the second matching points 62 may be a starting point, a highest point, a lowest point, or a point at a position of a maximum curvature radius on the second fracture curve as well. The plurality of first matching points 52 and the plurality of second matching points 62 are matched with each other one-to-one. Generally, the starting point on the first fracture curve corresponds to the starting point on the second fracture curve, the highest point on the first fracture curve corresponds to the lowest point on the second fracture curve, and vice versa; and the point at the position of the maximum curvature radius on the first fracture curve corresponds to the point at the position of the maximum curvature radius on the second fracture curve.

Further through the image processing, a plurality of third matching points 72 are obtained on the third matching curve 71, and the third matching points 72 may be a starting point, a highest point, a lowest point, or a point at a position of a maximum curvature radius on the third fracture curve, etc. A plurality of fourth matching points 82 are obtained on the fourth matching curve 81, and the fourth matching points 82 may be a starting point, a highest point, a lowest point, or a point at a position of a maximum curvature radius on the fourth fracture curve, etc. The plurality of third matching points 72 and the plurality of fourth matching points 82 are matched with each other one-to-one. Generally, the starting point on the third fracture curve corresponds to the starting point on the fourth fracture curve, the highest point on the third fracture curve corresponds to the lowest point on the fourth fracture curve, and vice versa; and the point at the position of the maximum curvature radius on the third fracture curve corresponds to the point at the position of the maximum curvature radius on the fourth fracture curve.

Next, first straight-line distances between the respective first matching points 52 and the respective corresponding second matching points 62 in the first axial direction 91 (x-axis) are calculated. A plurality of first matching points 52 and a plurality of second matching points 62 will inevitably form a plurality of first straight-line distances. A first average value of the plurality of first straight-line distances is calculated.

Second straight-line distances between the respective first matching points 52 and the respective corresponding second matching points 62 in a second axial direction (y-axis) are calculated. The plurality of first matching points 52 and the plurality of second matching points 62 will inevitably form a plurality of second straight-line distances. A second average value of the plurality of second straight-line distances is calculated.

Third straight-line distances between the respective third matching points 72 and the respective corresponding fourth matching points 82 in the second axial direction (y-axis) are calculated. A plurality of third matching points 72 and a plurality of fourth matching points 82 will inevitably form a plurality of third straight-line distances. A third average value of the plurality of third straight-line distances is calculated.

Fourth straight-line distances between the respective third matching points 72 and the respective corresponding fourth matching points 82 in the third axial direction 92 (z-axis) are calculated. The plurality of third matching points 72 and the plurality of fourth matching points 82 will inevitably form a plurality of fourth straight-line distances. A fourth average value of the plurality of fourth straight-line distances is calculated.

The safety-limit zone is determined as a cuboid with a center point being the coordinate origin point, a length side of the cuboid is parallel to the first axial direction 91, and a length value of the cuboid is greater than or equal to the first average value. The length value of the cuboid may be greater than the first average value by 2 mm-3 mm. A width side of the cuboid is parallel to the second axial direction, a width value of the cuboid is greater than or equal to the second average value or the third average value, and generally, a larger one of the second average value and the third average value is selected for subsequent calculation, so as to form a relatively-large safety-limit zone. The width value of the cuboid may be greater than the second average value or the third average value by 2 mm-3 mm. A height side of the cuboid is parallel to the third axial direction 92, and a height value of the cuboid is greater than or equal to the fourth average value. The height value of the cuboid may be greater than the fourth average value by 2 mm-3 mm.

The determination of the safety-limit zone is described in detail above, and the determination of the safety-rotation angles is described in detail below.

Referring to FIG. 2 and FIG. 3, a first inclination angle $\beta e$ of a first boundary-line segment connected with the first matching curve 51 relative to the first axial direction 91 is obtained on the first effective area 5. A second inclination angle $\beta s$ of a second boundary-line segment connected with the second matching curve 61 relative to the first axial direction 91 is obtained on the second effective area 6, and the first boundary-line segment and the second boundary-line segment are capable of being matched as one line segment. For example, if the first boundary-line segment is located on a left side of the first effective area 5, the second boundary-line segment is located on a left side of the second effective area 6 as well. If the first boundary-line segment is located on a right side of the first effective area 5, the second boundary-line segment is located on a right side of the second active area 6 as well. The first boundary-line segment and the second boundary-line segment are capable of being matched as one line segment, which means that the first boundary-line segment and the second boundary-line segment are capable of being connected to form one line segment after fractured parts are reset.

A third inclination angle $\theta e$ of a third boundary-line segment connected with the third matching curve 71 relative to the third axial direction 92 is obtained on the third effective area 7. A fourth inclination angle $\theta s$ of a fourth boundary-line segment connected with the fourth matching curve 81 relative to the third axial direction 92 is obtained on the fourth effective area 8, and the third boundary-line segment and the fourth boundary-line segment are capable of being matched as one line segment. For example, if the third boundary-line segment is located on a left side of the third effective area 7, the fourth boundary-line segment is located on a left side of the fourth effective area 8 as well. If the third boundary-line segment is located on a right side of the third effective area 7, the fourth boundary-line segment is located on a right side of the fourth active area 8 as well. The third boundary-line segment and the fourth boundary-line segment are capable of being matched as one line segment, which means that the third boundary-line segment and the fourth boundary-line segment are capable of being connected to form one line segment after fractured parts are reset The first boundary-line segment, the second boundary-line segment, the third boundary-line segment and the fourth boundary-line segment are all images formed by edges of the bones themselves. Since the fracture may produce a dislocation angle with a certain angle value, the reset needs rotation to eliminate the dislocation angle.

Figure 6:
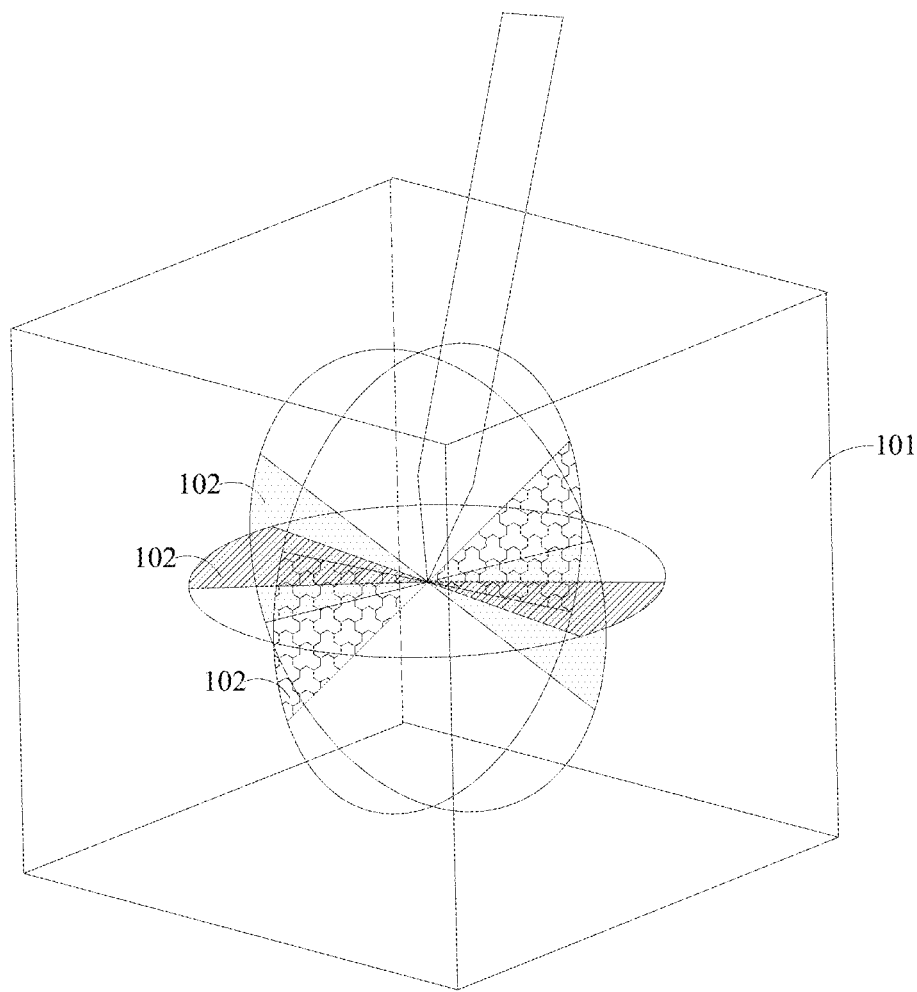
FIG. 6 is a structural diagram that schematically shows a formed safety-limit zone and safety-rotation angles.

It is determined that an absolute value of a difference value between the first inclination angle and the second inclination angle is equal to or less than the safety-rotation angle relative to the third axial direction 92. The safety-rotation angle may be 105%-110% of the absolute value of the difference value between the first inclination angle and the second inclination angle. An absolute value of a difference value between the third inclination angle and the fourth inclination angle is equal to or less than the safety-rotation angle relative to the first axial direction 91. The safety-rotation angle may be 105%-110% of the absolute value of the difference value between the third inclination angle and the fourth inclination angle. Thus, the safety-limit zone 101 and the safety-rotation angles 102 as shown in FIG. 6 are obtained.

Figure 4:
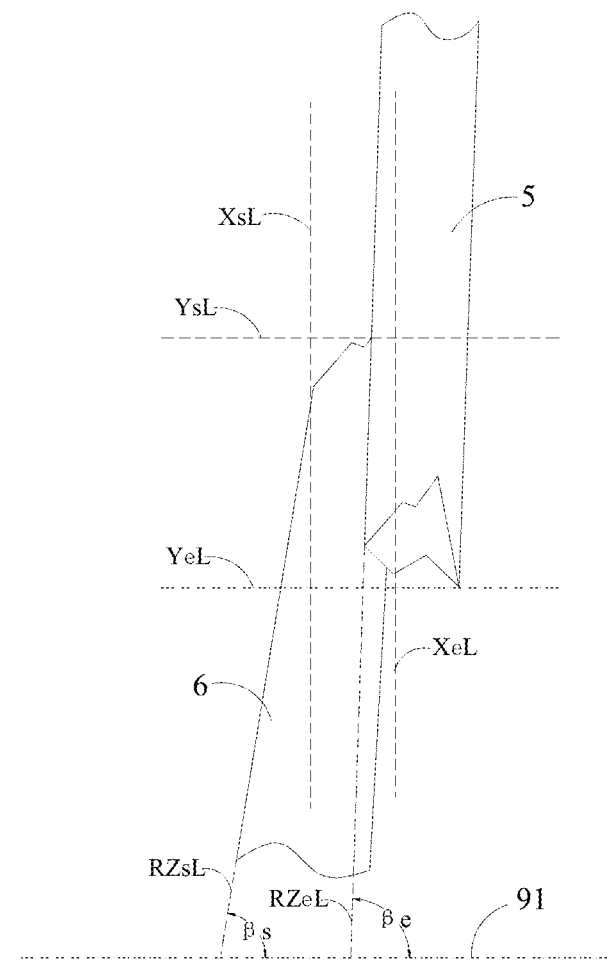
FIG. 4 is a Computed Tomography (CT) image that schematically shows processing on the first image.

In other exemplary embodiments of the present disclosure, referring to FIG. 4, medical staffs may directly draw boundary lines of a safety area on the first image according to their own years of experience (wherein a firstly-drawn line or starting line is startLine (indicated by a subscript sL), and a later-drawn line or ending line is endLine (indicated by a subscript eL)). XsL is a vertical line with a x-axis coordinate (Xs, 0) aligned with a bone boundary at a position where the reset is to start. XeL is a vertical line with a x-axis coordinate (Xe, 0) aligned with the bone boundary at a position where the reset is to end, and considering elasticity of muscles and dislocation of skin, this line will exceed the bone boundary by a distance of 2-3 mm. YsL is a horizontal line with a y-axis coordinate (0, Ys) aligned with a bone boundary at a position where the reset is to start. YeL is a horizontal line with a y-axis coordinate (0, Ye) aligned with the bone boundary at a position where the reset is to end, and considering elasticity of muscles and dislocation of skin, this line will exceed the bone boundary by a distance of 2-3 mm. RZsL is an oblique line with an included angle of $\beta s$ from x-axis and aligned with a bone boundary at a position where the reset is to start. RZeL is an oblique line with an included angle of $\beta e$ from x-axis and aligned with the bone boundary at a position where the reset is to end, and considering elasticity of muscles and dislocation of skin, the angle of this line will be larger than that of an actual bone boundary by 5%-10%. After the medical staffs complete the drawing, a system adopting the method for determining a safety-limit zone of the present disclosure automatically calculates a maximum movement range, $\Delta x = Xe - Xs$, $\Delta y = Ye - Ys$, $\Delta rz = \beta e - \beta s$, allowed to reset the fracture.

Figure 5:
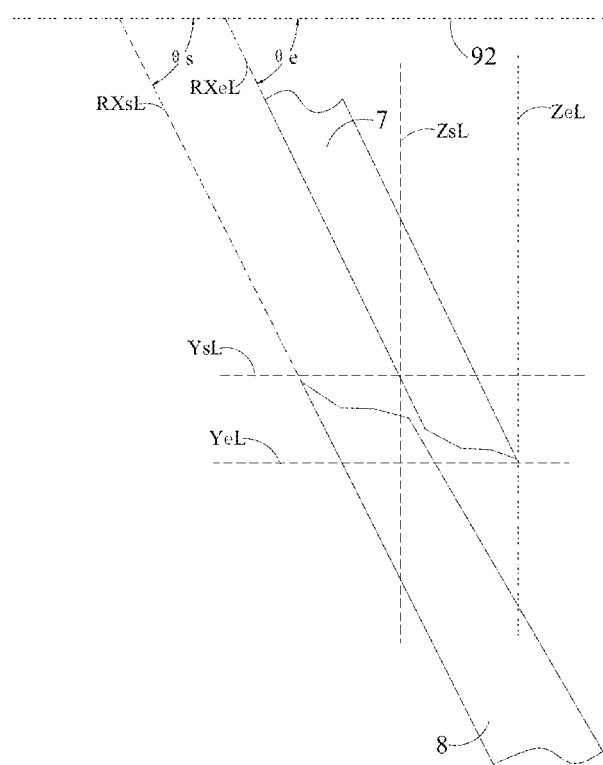
FIG. 5 is a CT image that schematically shows processing on the second image.

Referring to FIG. 5, the medical staffs may directly draw boundary lines of a safety area on the second image according to their own years of experience (wherein a firstly-drawn line or starting line is startLine (indicated by a subscript sL), and a later-drawn line or ending line is endLine (indicated by a subscript eL)). ZsL is a vertical line with a z-axis coordinate (Zs, 0) aligned with a bone boundary at a position where the reset is to start. ZeL is a vertical line with a z-axis coordinate (Ze, 0) aligned with the bone boundary at a position where the reset is to end, and considering elasticity of muscles and dislocation of skin, this line will exceed the bone boundary by a distance of 2-3 mm. YsL is a horizontal line with a y-axis coordinate (0, Ys) aligned with a bone boundary at a position where the reset is to start. YeL is a horizontal line with a y-axis coordinate (0, Ye) aligned with the bone boundary at a position where the reset is to end, and considering elasticity of muscles and dislocation of skin, this line will exceed the bone boundary by a distance of 2-3 mm. RXsL is an oblique line with an included angle of θs from z-axis and aligned with a bone boundary at a position where the reset is to start. RXeL is an oblique line with an included angle of θe from z-axis and aligned with the bone boundary at a position where the reset is to end, and considering elasticity of muscles and dislocation of skin, the angle of this line will be larger than that of an actual bone boundary by 5%-10%. After the medical staffs complete the drawing, the system adopting the method for determining a safety-limit zone of the present disclosure automatically calculates a maximum movement range, $\Delta z=Ze-Zs$, $\Delta y=Ye-Ys$, $\Delta rx=\theta e-\theta s$, allowed to reset the fracture. $\Delta y$ may take a larger one, and $\Delta ry$ may take 0, such that the safety-limit zone (Safe Area) 101 and the safety-rotation angles 102 ($\Delta x$, $\Delta y$, $\Delta z$, $\Delta rx$, $\Delta ry$, $\Delta rz$) may be obtained, as shown in FIG. 6.

Additionally, although the respective steps of the method of the present disclosure are depicted in the figure in a particular order, this does not require or imply that the steps must be performed in the particular order or that the desired result may be achieved only if all illustrated steps are performed. Additionally or alternatively, certain steps may be omitted, a plurality of steps may be combined into one step for execution, and/or one step may be decomposed into a plurality of steps for execution, etc.

Figure 7:
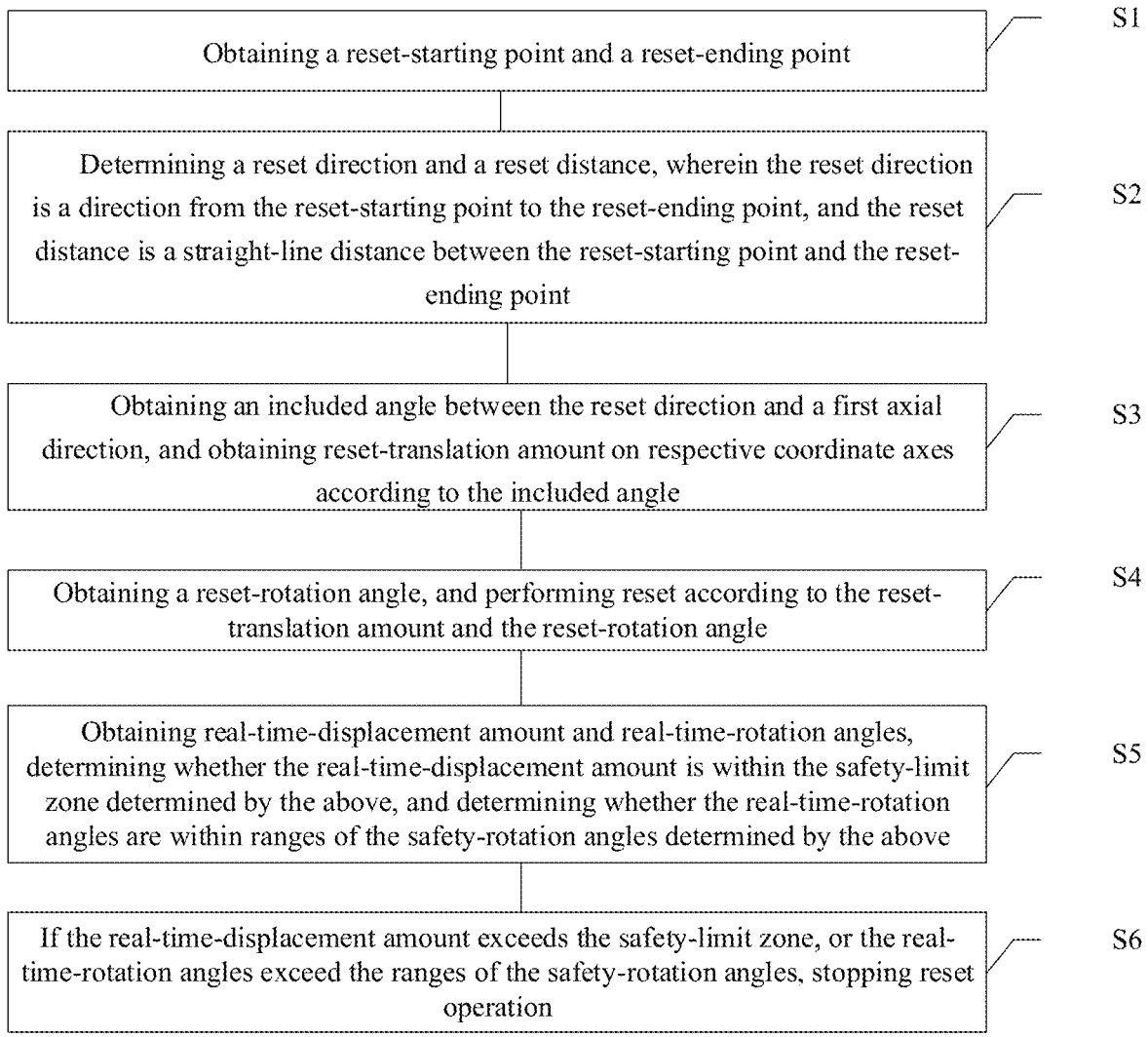
FIG. 7 is a flow chart that schematically shows an exemplary embodiment of a reset method of the present disclosure.

Further, the exemplary embodiment further provides a reset method. Referring to FIG. 7, the reset method may include the following steps:

step S1, obtaining a reset-starting point and a reset-ending point;

step S2, determining a reset direction and a reset distance, wherein the reset direction is a direction from the reset-starting point to the reset-ending point, and the reset distance is a straight-line distance between the reset-starting point and the reset-ending point;

step S3, obtaining included angles θ between the reset direction and respective coordinate axes, and obtaining reset-translation amount on respective coordinate axes according to the included angles θ;

step S4, obtaining respective reset-rotation angles β, and performing reset operation according to the reset-translation amount and the respective reset-rotation angles β;

step S5, obtaining real-time-displacement amount and real-time-rotation angles, determining whether the real-time-displacement amount is within the above-determined safety-limit zone, and determining whether the real-time-rotation angles are within ranges of the above-determined safety-rotation angles; and step S6, in response to the real-time-displacement amount exceeds the safety-limit zone, or the real-time-rotation angles exceed the ranges of the safety-rotation angles, stopping the reset operation.

First of all, it is necessary to establish a connection between a remote computer and a robot, which may adopt a Socket communication manner. The computer sends instructions to the robot through a socket. At the same time, an separate thread threadMonitor is created on the computer to monitor position information of the robot in real time (x, y, z, rx, ry, rz).

The robot is remotely set to be in a free-moving state, and a doctor may drag the robot to contact a limb of a fractured patient, and place the robot and the patient in a suitable position, that is, at this time, angles of respective joints of the robot are as close as possible to 0 degrees, such that the robot may have a larger manipulative space, then free-moving state is lifted, the robot holds the limb of the patient and keeps it still, and the system records an original position of the robot, OriginalPoint (X0, Y0, Z0, RX0, RY0, RZ0).

In the exemplary embodiment, the medical staffs may input the reset-starting point and the reset-ending point in the first image. Generally, a first-input point is the reset-starting point, and a later-input point is the reset-ending point. Of course, they may be input in set menu options.

Figure 8:
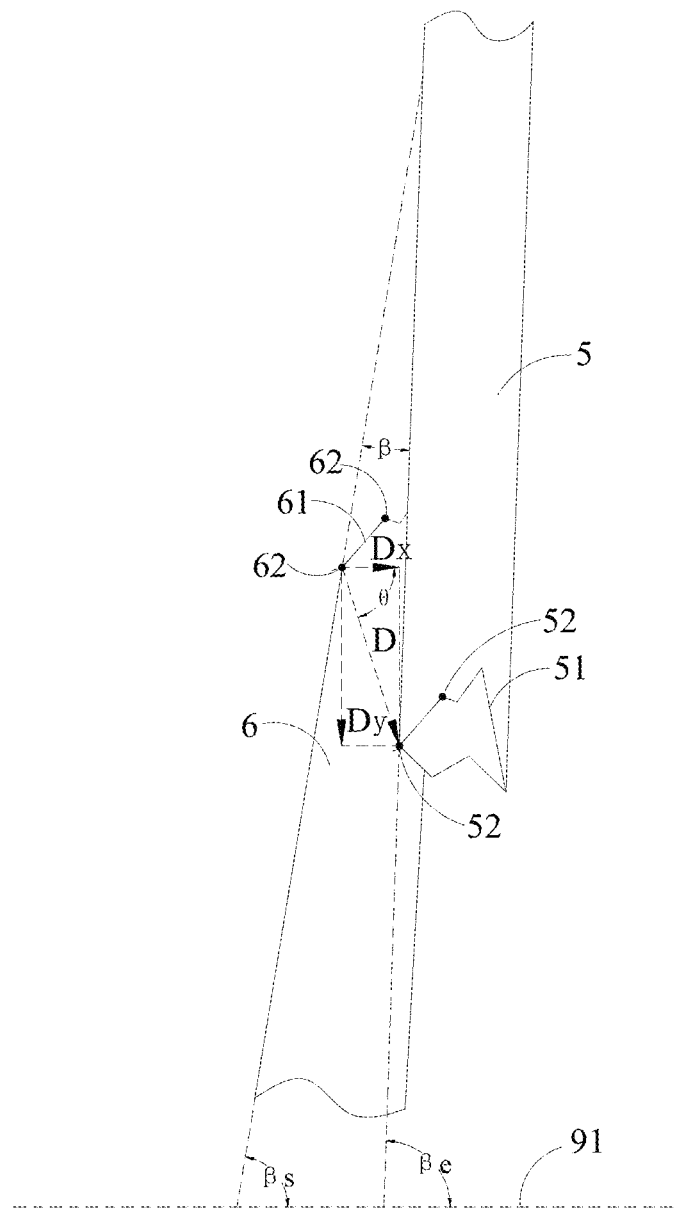
FIG. 8 is a structural diagram that schematically shows inputting on the first image during reset.

As shown in FIG. 8, an arrow direction in the figure represents the reset direction, and a straight-line length D represents the reset distance. After the reset direction is determined, the included angle θ between the reset direction and the first axial direction 91 (the axis where Dx is located in the figure, other axes are similar) may be automatically obtained, and then decomposed reset-translation amount of the x-axis and z-axis are $\Delta x=Dx=D*\sin\theta$, $\Delta y=Dy=D*\cos\theta$.

The reset-rotation angle β may be input by the medical staffs in the first image, and converted into radians as $\Delta rz=\beta*3.14/180$. After the reset-translation amount and reset-rotation angle are determined, coordinates of a target point (X0+D*sin θ, Y0+D*cos θ, Z0, RX0, RY0, RZ0+β*3.14/180) may be automatically generated. The robot may execute Move1 (X0+D*sin θ, Y0+D*cos θ, Z0, RX0, RY0, RZ0+β*3.14/180).

During reset process, the real-time-displacement amount and real-time-rotation angles are obtained, and it is determined whether the real-time-displacement amount is within the above-determined safety-limit zone, and whether the real-time-rotation angles are within the ranges of the above-determined safety-rotation angles.

If the real-time-displacement amount exceeds the safety-limit zone, or the real-time-rotation angles exceed the ranges of the above-determined safety-rotation angles, the reset operation is stopped. If the real-time-displacement amount does not exceed the safety-limit zone, and the real-time-rotation angles do not exceed the ranges of the above-determined safety-rotation angles, the reset operation is continued until the reset is completed.

Figure 9:
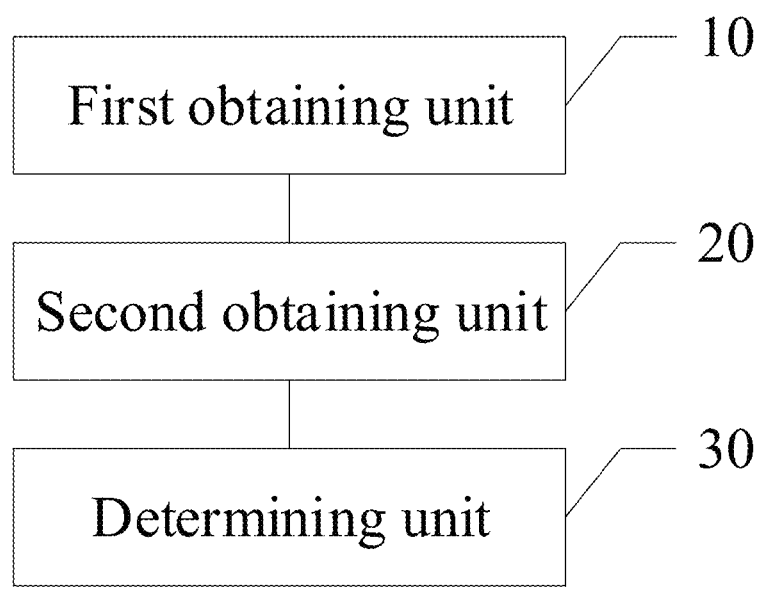
FIG. 9 is a block diagram that schematically shows an exemplary embodiment of a device for determining a safety-limit zone of the present disclosure.

Further, the exemplary embodiment further provides a device for determining a safety-limit zone corresponding to the above-mentioned method for determining a safety-limit zone. Referring to FIG. 9, the device for determining a safety-limit zone may include a first obtaining unit 10, the second obtaining unit 20 and a determining unit 30. The first obtaining unit 10 may be used to obtain the first image from the limb taken from the first direction, the first image includes the first effective area 5 and the second effective area 6, and the first effective area 5 is capable of matching with the second effective area 6. The second obtaining unit 20 may be used to obtain the second image from the limb taken from the second direction, the second image includes the third effective area 7 corresponding to the first effective area 5, and the fourth effective area 8 corresponding to the second effective area 6, the third effective area 7 is capable of matching with the fourth effective area 8, and the second direction and the first direction are perpendicular to each other. The determining unit 30 may obtain the safety-limit zone and the safety-rotation angles according to the first effective area 5, the second effective area 6, the third effective area 7 and the fourth effective area 8.

Specific details of respective modules in the above device for determining a safety-limit zone have been described in detail in the corresponding method for determining a safety-limit zone, and therefore will not be repeated here.

Figure 10:
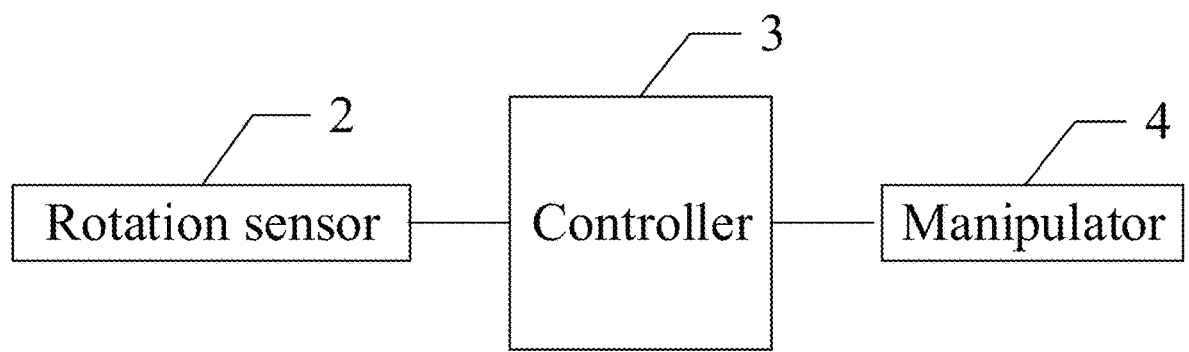
FIG. 10 is a block diagram that schematically shows an exemplary embodiment of a robot of the present disclosure.
Figure 11:
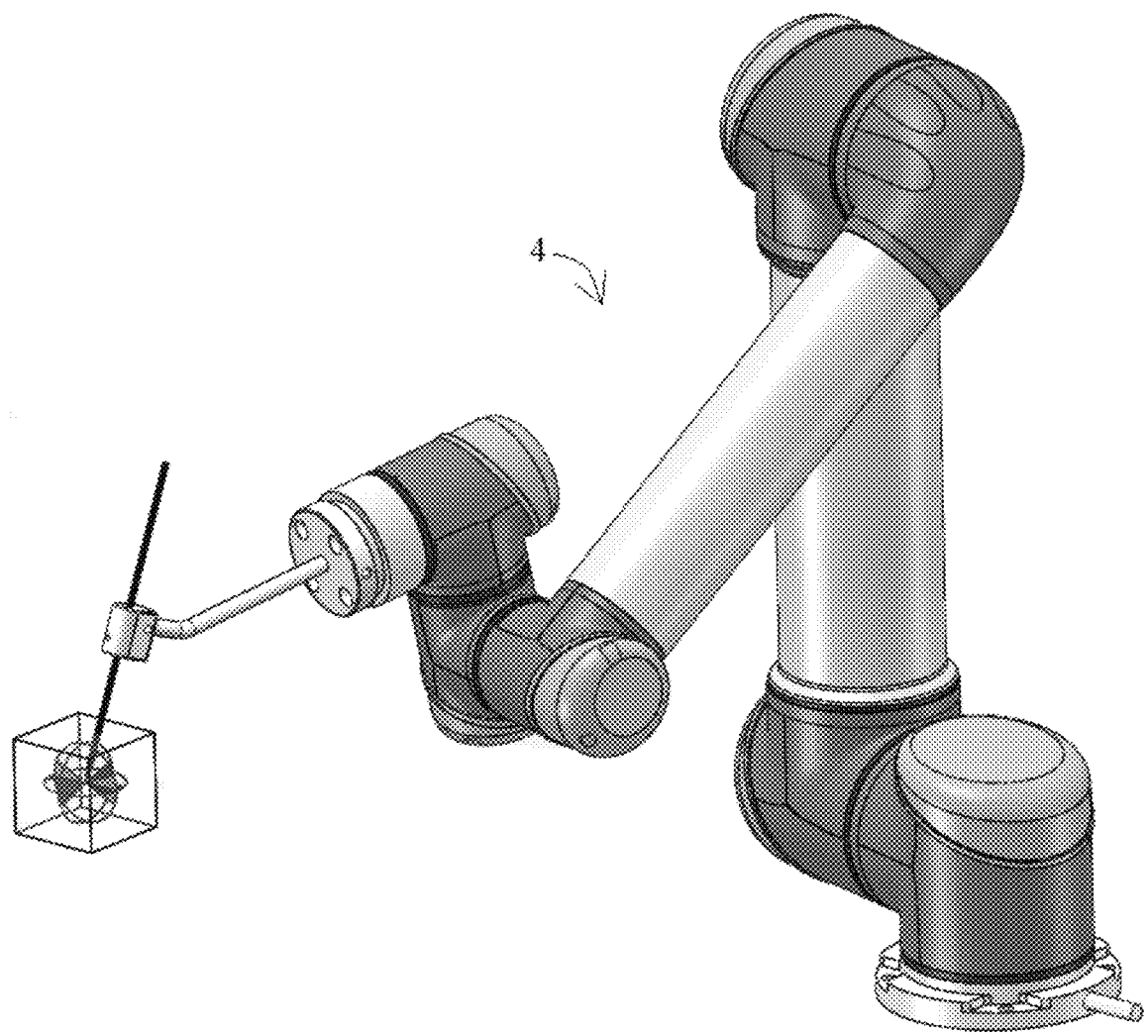
FIG. 11 is a structural diagram that schematically shows an exemplary embodiment of a robot of the present disclosure.

Further, the exemplary embodiment further provides a medical robot. Referring to FIG. 10 and FIG. 11, the medical robot may include a manipulator 4, a rotation sensor 2, a controller 3 and the above-mentioned device for determining a safety-limit zone, wherein the device for determining a safety-limit zone may be located in the controller 3, for example. The device for determining a safety-limit zone has been described in detail above, so it will not be repeated here.

The rotation sensor 2 may be used to measure real-time-rotation angles of the manipulator 4. An input end of the controller 3 is electrically connected to an output end of the rotation sensor 2. The controller 3 may calculate to obtain real-time displacement amount of the manipulator 4 according to the real-time-rotation angles of the manipulator 4 measured by the rotation sensor 2. An output end of the controller 3 is electrically connected to a control end of the manipulator 4. The controller 3 may be used to control start and stop of the manipulator 4 according to measurement values of the rotation sensor 2, and the safety-limit zone and the safety-rotation angles determined by the device for determining a safety-limit zone. The controller 3 may be provided on a remote computer.

In other exemplary embodiments of the present disclosure, a doctor does not need to draw on the image, but directly presses move buttons on an operation interface (the buttons may control the robot to move and rotate along directions such as X+, X−, Y+, Y−, RX+, RX−, RY+, RY−, RZ+, RZ−, and so on). The robot continues to move in a specific direction, at the same time, the thread threadMonitor continues to trigger an security module to determine whether the robot has reached safety boundaries, and if not, it is allowed to continue to move, if it does, the robot will be locked immediately, and stop moving. Usually, before reaching the safety boundary, the bones will return to their original positions. After the doctor observes that the bones have returned to their original positions, the doctor may just release the button to actively stop movement of the robot.

During the reset performed by the robot, the images will be refreshed at a certain frequency, and the doctor can observe reset effect in real time.

It should be noted that although several modules or units of a device for performing actions are mentioned in the above detailed description, this division is not mandatory. In fact, according to embodiments of the present disclosure, the features and functions of two or more modules or units described above may be embodied in one module or unit. Conversely, the features and functions of one module or unit described above may be further divided into a plurality of modules or units to be embodied.

From the description of the above embodiments, those skilled in the art can easily understand that the exemplary embodiments described herein may be implemented by software, or may be implemented by software combined with necessary hardware. Therefore, the technical solution according to the embodiments of the present disclosure may be embodied in the form of a software product, and the software product may be stored in a non-volatile storage medium (which may be a CD-ROM, U disk, mobile hard disk, etc.) or on a network, including several instructions to cause a computing device (which may be a personal computer, a server, a mobile terminal, or a network device, etc.) to execute the method according to an embodiment of the present disclosure.

Other embodiments of the present disclosure will readily occur to those skilled in the art upon consideration of the specification and practice of the disclosure disclosed herein. This application is intended to cover any variations, uses, or adaptations of the present disclosure that follow the general principles of the present disclosure and include common knowledge or techniques in the technical field not disclosed by the present disclosure. The specification and examples are to be regarded as exemplary only, and true scope and spirit of the disclosure is indicated by the appended claims.

What is claimed is:

1. A method for determining a safety-limit zone, comprising:
    obtaining a first image from a limb taken from a first direction, wherein the first image comprises a first effective area and a second effective area, and the first effective area is capable of matching with the second effective area;
    obtaining a second image from the limb taken from a second direction, wherein the second image comprises a third effective area corresponding to the first effective area, and a fourth effective area corresponding to the second effective area, the third effective area is capable of matching with the fourth effective area, and the second direction and the first direction are perpendicular to each other; and
    obtaining a safety-limit zone and safety-rotation angles according to the first effective area, the second effective area, the third effective area and the fourth effective area,
    the step of obtaining a safety-limit zone and safety-rotation angles according to the first effective area, the second effective area, the third effective area and the fourth effective area, comprises:
    establishing a three-dimensional-rectangular-coordinate system with a coordinate origin point that is a contact point between a manipulator and the limb;
    obtaining a first matching curve matching with the second effective area on the first effective area, and obtaining a second matching curve matching with the first effective area on the second effective area;
    obtaining a plurality of first matching points on the first matching curve, and obtaining a plurality of second matching points on the second matching curve, wherein the plurality of first matching points and the plurality of second matching points are matched to each other one-to-one;
    obtaining a third matching curve matching with the fourth effective area on the third effective area, and obtaining a fourth matching curve matching with the third effective area on the fourth effective area;
    obtaining a plurality of third matching points on the third matching curve, and obtaining a plurality of fourth matching points on the fourth matching curve, wherein the plurality of third matching points and the plurality of fourth matching points are matched to each other one-to-one; and
    obtaining the safety-limit zone according to the plurality of first matching points, the plurality of second matching points, the plurality of third matching points and the plurality of fourth matching points.

2. The method for determining a safety-limit zone according to claim 1, wherein the step of obtaining the safety-limit zone according to the plurality of first matching points, the plurality of second matching points, the plurality of third matching points and the plurality of fourth matching points, comprises:
    calculating first straight-line distances between the respective first matching points and the corresponding respective second matching points on a first axial direction, and calculating a first average value of the first straight-line distances;

calculating second straight-line distances between the respective first matching points and the corresponding respective second matching points on a second axial direction, and calculating a second average value of the second straight-line distances;

calculating third straight-line distances between the respective third matching points and the corresponding respective fourth matching points on the second axial direction, and calculating a third average value of the third straight-line distances;

calculating fourth straight-line distances between the respective third matching points and the corresponding respective fourth matching points on a third axial direction, and calculating a fourth average value of the fourth straight-line distances; and determining the safety-limit zone as a cuboid with a center point being the coordinate origin point, wherein a length side of the cuboid is parallel to the first axial direction, a length value of the cuboid is greater than or equal to the first average value, a width side of the cuboid is parallel to the second axial direction, a width value of the cuboid is greater than or equal to the second average value or the third average value, a height side of the cuboid is parallel to the third axial direction, and a height value of the cuboid is greater than or equal to the fourth average value.

3. The method for determining a safety-limit zone according to claim 2, wherein the second average value is greater than the third average value, and the width value of the cuboid is greater than or equal to the second average value.

4. The method for determining a safety-limit zone according to claim 3, wherein the length value of the cuboid is larger than the first average value by 2-3 mm, the width value of the cuboid is larger than the second average value by 2-3 mm, and the height value of the cuboid is greater than the fourth average value by 2-3 mm.

5. The method for determining a safety-limit zone according to claim 2, wherein the step of obtaining safety-rotation angles according to the first effective area, the second effective area, the third effective area and the fourth effective area, comprises:

obtaining a first inclination angle of a first boundary-line segment connected with the first matching curve relative to the first axial direction on the first effective area;

obtaining a second inclination angle of a second boundary-line segment connected with the second matching curve relative to the first axial direction on the second effective area, wherein the first boundary-line segment and the second boundary-line segment are capable of being matched as one line segment;

obtaining a third inclination angle of a third boundary-line segment connected with the third matching curve relative to the third axial direction on the third effective area;

obtaining a fourth inclination angle of a fourth boundary-line segment connected with the fourth matching curve relative to the third axial direction on the fourth effective area, wherein the third boundary-line segment and the fourth boundary-line segment are capable of being matched as one line segment; and determining that an absolute value of a difference value between the first inclination angle and the second inclination angle is equal to or less than the safety-rotation angle relative to the third axial direction, and an absolute value of a difference value between the third inclination angle and the fourth inclination angle is equal to or less than the safety-rotation angle relative to the first axial direction.

6. The method for determining a safety-limit zone according to claim 5, wherein the safety-rotation angle relative to the third axial direction is 105%-110% of the absolute value of the difference value between the first inclination angle and the second inclination angle, and the safety-rotation angle relative to the first axial direction is 105%-110% of the absolute value of the difference value between the third inclination angle and the fourth inclination angle.

7. A reset method, comprising:

obtaining a reset-starting point and a reset-ending point;

determining a reset direction and a reset distance, wherein the reset direction is a direction from the reset-starting point to the reset-ending point, and the reset distance is a straight-line distance between the reset-starting point and the reset-ending point;

obtaining included angles between the reset direction and respective coordinate axes, and obtaining reset-translation amount on respective coordinate axes according to the included angles;

obtaining reset-rotation angles, and performing reset operation according to the reset-translation amount and the respective reset-rotation angles;

obtaining real-time-displacement amount and real-time-rotation angles, determining whether the real-time-displacement amount is within the safety-limit zone determined by the method for determining a safety-limit zone according to claim 1, and determining whether the real-time-rotation angles are within ranges of the safety-rotation angles determined by the method for determining a safety-limit zone according to claim 1; and in response to the real-time-displacement amount exceeds the safety-limit zone, or the real-time-rotation angles exceed the ranges of the safety-rotation angles, stopping the reset operation.

8. A device for determining a safety-limit zone, comprising:

a first obtaining unit, configured to obtain a first image from a limb taken from a first direction, wherein the first image comprises a first effective area and a second effective area, and the first effective area is capable of matching with the second effective area;

a second obtaining unit, configured to obtain a second image from the limb taken from a second direction, wherein the second image comprises a third effective area corresponding to the first effective area, and the fourth effective area corresponding to the second effective area, the third effective area is capable of matching with the fourth effective area, and the second direction and the first direction are perpendicular to each other; and a determining unit, configured to obtain a safety-limit zone and safety-rotation angles according to the first effective area, the second effective area, the third effective area and the fourth effective area, wherein the determining unit is further configured to:

establish a three-dimensional-rectangular-coordinate system with a coordinate origin point that is a contact point between a manipulator and the limb;

obtain a first matching curve matching with the second effective area on the first effective area, and obtain a second matching curve matching with the first effective area on the second effective area;

obtain a plurality of first matching points on the first matching curve, and obtain a plurality of second matching points on the second matching curve, wherein the plurality of first matching points and the plurality of second matching points are matched to each other one-to-one;

obtain a third matching curve matching with the fourth effective area on the third effective area, and obtain a fourth matching curve matching with the third effective area on the fourth effective area;

obtain a plurality of third matching points on the third matching curve, and obtain a plurality of fourth matching points on the fourth matching curve, wherein the plurality of third matching points and the plurality of fourth matching points are matched to each other one-to-one; and obtain the safety-limit zone according to the plurality of first matching points, the plurality of second matching points, the plurality of third matching points and the plurality of fourth matching points.

9. A medical robot, comprising:

a manipulator;

the device for determining a safety-limit zone according to claim 8;

a rotation sensor, configured to measure real-time-rotation angles of the manipulator; and a controller, having an input end electrically connected to an output end of the rotation sensor, and an output end electrically connected to a control end of the manipulator, wherein the controller is configured to control start and stop of the manipulator according to measurement values of the rotation sensor, and a safety-limit zone and safety-rotation angles determined by the device for determining a safety-limit zone.

\* \* \* \* \*